United States Patent [19]

Kolesov et al.

[11] 4,350,160
[45] Sep. 21, 1982

[54] INSTRUMENT FOR ESTABLISHING VASCULAR ANASTOMOSES

[76] Inventors: Evgeny V. Kolesov, prospekt Veteranov, 151, korpus 2, kv. 52, Leningrad; Boris A. Smirnov, ulitsa Borisa Galushkina, 17, kv. 26; Vladimir M. Fedotov, ulitsa Startovaya, 21, kv. 42, both of Moscow; Iosif L. Lipovsky, Ozerkovsky prospekt, 7, kv. 2, Leningrad, all of U.S.S.R.

[21] Appl. No.: 136,736

[22] Filed: Apr. 2, 1980

[30] Foreign Application Priority Data

Nov. 14, 1979 [SU] U.S.S.R. .............................. 2833451

[51] Int. Cl.³ ...................... A61B 17/04; A61B 17/12; A61B 17/08; B31B 1/00
[52] U.S. Cl. ................................ 128/334 R; 128/325; 128/335; 227/19; 227/DIG. 1; 227/156
[58] Field of Search ................... 128/325, 334 R, 335, 128/334 C, 346; 227/19, DIG. 1, 156

[56] References Cited

U.S. PATENT DOCUMENTS

| 3,040,748 | 6/1962 | Klein et al. | 128/334 R |
|---|---|---|---|
| 3,111,124 | 11/1963 | Rodbard | 128/346 |
| 3,144,654 | 8/1964 | Mallina et al. | 128/334 R |
| 3,638,652 | 2/1972 | Kelly | 128/334 R |
| 3,833,002 | 9/1974 | Palma | 128/334 R |
| 3,916,905 | 11/1975 | Kuhn | 128/334 R |
| 3,960,151 | 6/1976 | Kuhn | 128/334 R |

FOREIGN PATENT DOCUMENTS 91447 1/1951 U.S.S.R. .
446269 12/1975 U.S.S.R. .

Primary Examiner—Kyle L. Howell
Assistant Examiner—C. W. Shedd
Attorney, Agent, or Firm—Fleit & Jacobson

[57] ABSTRACT

The instrument has a separable body composed of two oblong interlinked members, each of them carrying at one of its vacant ends a detachable split bush adapted for the element being sutured to pass through the interior thereof and arranged across the longitudinal axis of the respective instrument body member. The bushes have flanges on the ends facing each other, each of the flanges having an open annular slot in the surfaces facing each other, and an opening made in the lateral face of the flange, the opening being communicated with the slot and with the tube that freely runs throughout the overall length of the instrument body and extends from it outwards so as to be connected to the vacuum device. The slots and openings in the bushes establish, along with the tubes, a system of air evacuation from the suturing zone, which is discarded along with the bush after the suturing procedure. One of the bushes has passages for the staples, while the other bush, a die for the staples to bend. A staple feeding mechanism is also provided.

2 Claims, 5 Drawing Figures

INSTRUMENT FOR ESTABLISHING VASCULAR ANASTOMOSES

The present invention relates to medical equipment and more specifically to a surgical instrument for establishing vascular anastomoses with the use of metallic staples, e.g., for circular suturing of blood vessels.

One prior-art instrument for circular suturing of blood vessels as covered by USSR Inventor's Certificate No. 91,447 (Int. Cl. A61b 17/11), is known to comprise a staple half having semirings and staple semibushes, a supporting half having semirings and supporting semibushes, a suturing lever-type actuator, and a device for holding the everted vessel ends. The instrument in question, however, suffers from a number of disadvantages, the cardinal one residing in that the instrument bushes should have an oblong shape, which requires high degree of liberation of the vessels to be anastomosed for preparing their ends and everting them upon the instrument bushes, which is far from being practicable in every particular case, especially when suturing coronary vessels. Moreover, vessels affected by sclerotic depositions on their walls, cannot be everted onto the semibushes by being folded back through 180°.

Some of these disadvantages are obviated in the instrument according to USSR Inventor's Certificate No. 446,269 (Int. Cl. A61b 17/11).

The instrument involved comprises a separable body, composed of two oblong hinge-joined members, each carrying at one of its ends a removable split bush adapted for passing the element being sutured through its interior, and situated across the longitudinal axis of the respective member of the instrument body.

The instrument has a permanent system of ducts for air evacuated from the suturing zone, formed by an annular slot in the body embracing the bush positioning site, said slot being communicated with tubes soldered to the body lengthwise the latter and adapted to define a negative pressure in the suturing zone so as to retain the elements being sutured in the everted position. Provision is also made for a mechanism feeding the staples through one of the bushes and a die for the staples to bend on the other bush, as well as a vacuum device communicated with the permanent system of ducts for air evacuation from the suturing zone.

Though the bushes are mounted detachably the system of air evacuation ducts remains to be permanent as being established by slots and tubes provided inside the instrument body and subject to clogging with blood clots during operation. That is why cleansing and sterilization of the instrument occurs to be difficult even after removing the bushes, and as a rule ineffective and inadequate, this being a substantial disadvantage of the instrument as being fraught with an instant danger for the patient in point of getting infected, communicating infection, etc.

Apart from that, on some occasions that occur rather frequently necessity arises of a repeated application of the instrument in the course of the same operation, which is the case when establishing a number of vascular anastomoses, in prompt surgery, etc. However, any rapid repeated application of the instrument is rendered impossible due to blocking the system of air evacuation from the suturing zone with blood clots, or due to an inadequate sterility of the system.

A primary and essential object of the present invention is therefore the provision of an instrument for establishing vascular anastomoses, which ensures guaranteed sterility, and a possibility of a rapid repeated use of the same instrument.

Another object of the present invention is to provide fast and reliable locking of the removable split bushes in the proposed instrument.

Among other objects of the present invention there are worth noting such as considerably less stringent requirements to the manufacturing accuracy of the components of the instrument suturing portion, reduced specific material consumption and cost of the instrument as a whole, as well as cut down labour expenses for manufacturing the instrument due to a simplified bush production technique.

One more object of the present invention is to provide convenience in handling the instrument and to improve liberation conditions for the vessels being sutured.

The abovesaid and other objects are accomplished due to the fact that in an instrument for establishing vascular anastomoses, comprising a separable body composed of two oblong interlinked members, each carrying at one of its ends a removable split bush adapted for passing the element being sutured through its interior and arranged across the longitudinal axis of the respective member of the body, a system of ducts for air evacuation from the suturing zone so as to define a negative pressure therein, that retains the elements being sutured in the everted position, a mechanism for feeding the staples through one of the bushes and a die for the staples to bend on the other bush, as well as a vacuum device communicated with the system of air evacuation ducts, according to the present invention, the bushes have flanges provided on the ends facing each other, each of said flanges having an open annular slot in their surfaces facing each other, and an opening is made in the face of each flange, said opening being communicated with said annular slot and with a tube freely passing throughout the overall length of the instrument body of the components thereof and extending from the instrument body outwards so as to be connected to the vacuum device, with the result that the slots and openings in the bushes form, along with the tubes, a system of air evacuation from the suturing zone, which can be discarded complete with the bush after the suturing procedure.

Provision of flanges on the bush ends facing each other makes it possible to define open annular slots therein and communicate said slots, via the side openings, with the tubes connected to the vacuum device, thus forming an air evacuation system. The bushes along with the air evacuation system are in effect single-use discardable components, which in turn contributes to guaranteed sterile conditions and renders the instrument rapidly reapplicable.

In one of the embodiments of the present invention the instrument body is provided with locating rods, while the flanges of the bushes have mating sockets adapted for an accurate positioning of the bushes in the instrument body, thereby providing for rapid and reliable locking of the bushes and the air evacuation system in the instrument.

In what follows the present invention will become more apparent in a description of a specific embodiment of an instrument for establishing vascular anastomoses, according to the invention, as a non-limiting illustrative example, to be considered with reference to the appended drawings, wherein.

Figure 1:
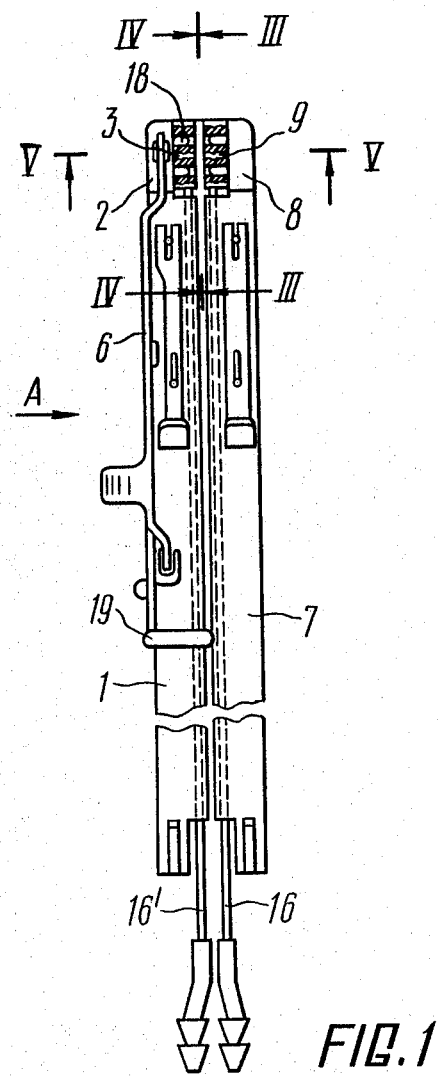
FIG. 1 is a general, partly sectional view of an instrument, according to the present invention.
Figure 2:
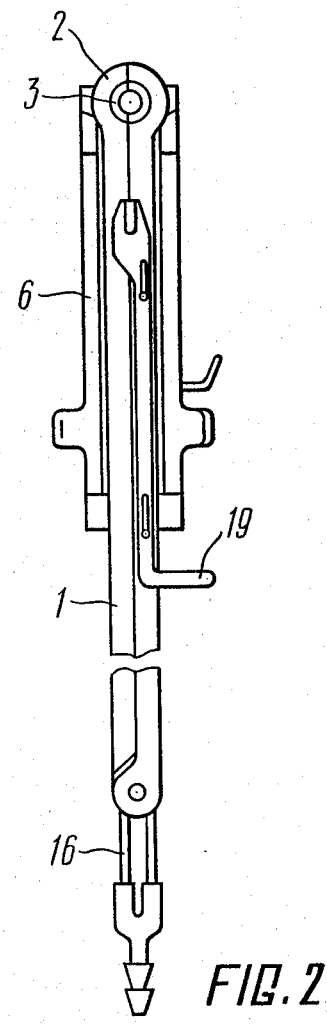
FIG. 2 is a side elevation view facing an arrow A in FIG. 1.
Figure 3:
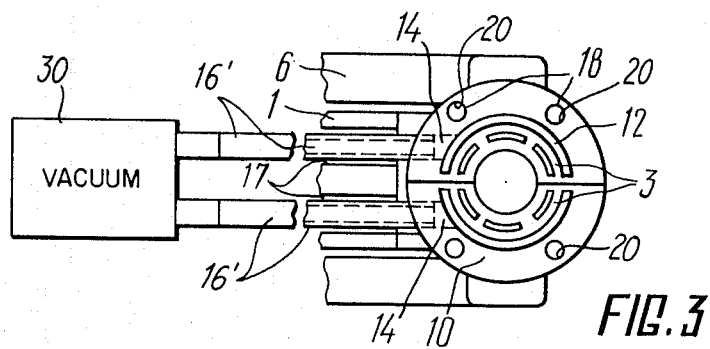
FIG. 3 is a section taken on the line III—III in FIG. 1.
Figure 4:
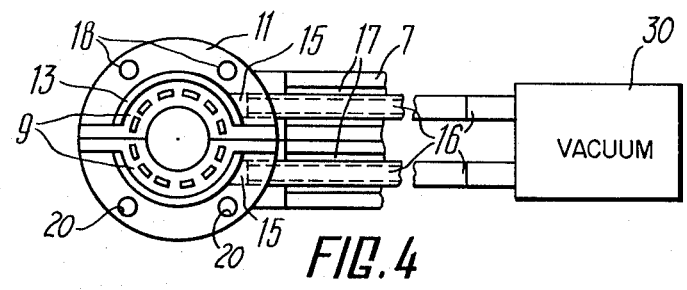
FIG. 4 is a section taken on the line IV—IV in FIG. 1.
Figure 5:
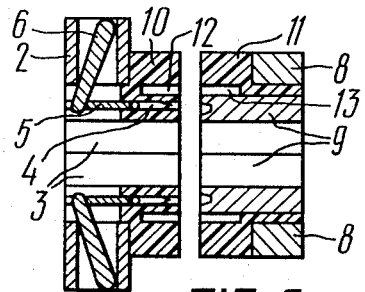
FIG. 5 is a section taken on the line V—V in FIG. 1.

An instrument of the invention is of a separable construction, composed of two members, i.e., a staple body 1 comprising two halves with semirings 2 (FIGS. 1, 2) and termed so because its semirings 2 carry a split staple bush 3 with staples 4 and ejectors 5 of the staples 4 (FIGS. 1, 5). The staple body 1 mounts also a mechanism for feeding the staples 4, provided with levers 6 (FIGS. 2, 3, 5). The other member of the instrument is a supporting body 7, comprising two halves with semirings 8 (FIGS. 1, 4) and termed so because its semirings 8 carry a split supporting bush 9 with a die for bending the staples 4. Upon having been ejected from the staple bush 3 the staples 4 thrust against the die of the split supporting bush 9 with their legs which are thus bent into the shape of the letter B to unite the tissues being sutured. The split staple bush 3 and supporting bush 9 have respective flanges 10 and 11 on the bush ends facing each other. The flange 10 of the staple bush 3 has an open annular slot 12 having a radius somewhat in excess of the radius of the slots for the staples 4, while the flange 11 of the supporting bush 9 has an open annular slot 13 with a radius somewhat in excess of the radius of recesses in the die of the supporting bush 9. The lateral faces of the flanges 10 and 11 have respective openings 14 and 15 communicated with the respective open annular slots 12 and 13. Tubes 16 and 16' (FIGS. 3, 4, 5) are connected to said respective openings 14 and 15, said tubes being laid in slots 17 along the halves of the staple body 1 and supporting body 7 and are connected with their opposite ends extending from the bodies 1 and 7 outwards, to the vacuum device 30. In order to provide fast, accurate and reliable locking of the staple bush 3 and supporting bush 9 in position, locating rods 18 are made on the semirings 2 and 8, while the flanges 10 and 11 have respective sockets 20 (FIGS. 3 and 4). A lock 19 (FIGS. 1, 2) is provided to join the supporting body 1 and the supporting body 7 together.

Now let us consider the operation of the instrument for establishing vascular anastomoses, according to the present invention.

Prior to starting operation one must open the package and take out the staple bush 3 and the supporting bush 9, both being in completely sterile condition, along with the tubes 16 and 16' mounted therein, the staple bush 3 being loaded with the staples 4 and provided with the ejectors 5 of the staples 4, fitted therein.

Then the staple bush 3 is put onto the rods 18 of the semirings 2 in the staple body 1, and the tubes 16, 16' are laid in the slots 17 and connected to the vacuum device. The supporting bush 9 is put onto the rods 18 of the semirings 8 in the supporting body 7, and the respective tubes 16 are laid in the slots 17 of the supporting body 7 and connected to the vacuum device 30 as well. Thus, the instrument is ready for operation.

The blood vessels to be united by suturing are passed through the bores of the bushes 3 and 9 by, say, setting apart the halves of the staple body 1, placing the vessel into the interior space of the bush 3 and bringing said halves together and locking them to each other, so that the vessel end should extend 3 to 4 mm from the flange 10 of the bush 3. Using the same techniques the other vessel is passed through the bore of the supporting bush 9 of the supporting body 7. Then the extending vessel ends are folded back with pincers towards the open annular slots 12 and 13 in the flanges 10 and 11 of the bushes 3 and 9. Folding back of the vessel ends and their approximating the annular slots 12 and 13 are accompanied by vacuum suction, whereby the vessel ends are everted and held to the bushes 3 and 9, intima outwards.

Next the surgeon must join the staple body 1 and the supporting body 7 together through the lock 19, with the result that the vessels are brought in contact with their intima, and the both ends of the sutured vessels are temporarily united. Then one must press the levers 6 of the mechanism for feeding the staples 4, thus actuating the ejectors 5 of the staples 4. As a result, both walls of the juxtaposed vessels fixed in a required position are pierced with the legs of the staples 4, which then get in the recesses of the die of the supporting bush 9 and are bent there into the shape of the letter B, thus stitching the vessel walls. The suturing over, the vacuum device is disconnected, the halves of the staple body 1 and supporting body 7 are set apart, and the instrument is removed from the sutured vessels.

The instrument of the invention for establishing vascular anastomoses is simple in construction and application techniques, is convenient and can be readily mastered by surgeons. It is of paramount importance that the instrument ensures high degree of sterility and quality of suturing operation and enables a number of repeated operations to be performed quickly within the same surgical intervention; in addition, the proposed instrument is much cheaper as compared to the known similar instruments.

What is claimed is:

1. A device for use with an instrument for establishing vascular anastomoses, said device comprising a first and second split bush, and an elongate tube connected to each of said split bushes so that the split bush and its associated tube form a detachably connectable unit;

said first and said second split bushes cooperating with each other to form a suturing zone, each of said split bushes being adapted to receive a vessel to be anastomosed through an interior space thereof and having a flange with a surface facing a surface of a flange of the other bush, one of said split bushes having a passage provided therein for passage of suturing staples, the other of said split bushes having a die for bending the suturing staples to thereby unite vessels being sutured, each of said flange facing surfaces having an annular slot formed therein, lateral faces of the flanges having openings formed therein in communication with said annular slots;

a first of said elongate tubes having one end connected to the opening in the flange of the first split bush; and a second of said elongate tubes having one end connected to the opening in the flange of the second split bush, other ends of said first and said second tubes being connectable to a source of negative pressure, the negative pressure suction attracting and holding ends of the vessels on said flange facing surfaces;

said instrument having first and second detachably joined oblong body members, each of said detachably connectable units being connectable to a respective one of said oblong body members, each of said oblong body members having a first end portion for receiving and for mounting one of said split bushes so that said split bushes form the suturing zone when the oblong body members are joined together, each of said oblong body members having a slot formed therein for receiving a respective one of said elongate tubes so that the other end of the elongate tube extends outward from a second end portion of said oblong body member.

2. A device according to claim 1, wherein each flange of each of said split bushes has a socket formed therein, each of said oblong body members having a locating rod engageable with a respective one of said sockets thereby ensuring accurate positioning of the split bushes with respect to the body members.

* * * * *